United States Patent [19]

van Andel

[11] Patent Number: Plant 6,785

[45] Date of Patent: May 9, 1989

[54] ALSTROEMERIA NAMED STADUTIA

[75] Inventor: Jacob van Andel, Aalsmeer, Netherlands

[73] Assignee: Van Staaveren B.V., Aalsmeer, Netherlands

[21] Appl. No.: 93,877

[22] Filed: Sep. 4, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of Alstroemeria plant characterized by its very large blooms, the petals of which are generally of a soft red coloration highlighted by the bright yellow coloration of the central body portion of the contiguous pair of the upper ones of the inside petals, which are deeply marked by longitudinal pencil stripes which extend upwardly from the base to the petal tip. This plant is further distinguished by its continuous year around blooming habit and its vigorous, strong growth, which reaches a height of up to about 200 cm., the flowers appearing singly on the branches of an umbel formation on a flower stem length of up to 150 to 200 cm., depending upon the season.

1 Drawing Sheet

BACKGROUND OF THE NEW PLANT

This new Alstroemeria variety originated as a seedling resulting from my crossing of a pair of Alstroemeria plants maintained in my greenhouse collection of plants for breeding purposes. This crossing was done at Aalsmeer, Holland, in 1982 with the object of producing plants having large red flowers, a strong growth habit, and good wintertime flower production. This particular seedling was selected fro propagation because it appeared to have the plant characteristics which I sought by my breeding efforts and asexual reproduction of this selected seedling was done by me and under my direction at Aalsmeer with very satisfactory results; and under my direction, propagation of this new variety was carried on through several successive generations, which demonstrated that the novel characteristics would hold true from generation to generation and appeared to be firmly fixed. The initial propagation of this plant was by its own roots and subsequent propagation was done by division of rhizomes. The present propagation of this new variety is done at Aalsmeer, Holland, by division of rhizomes.

DESCRIPTION OF THE DRAWING

This new variety of Alstroemeria plant is illustrated by the accompanying photographic drawing which, in full color, shows the flowers of a blooming umbel of the plant and demonstrates the flower form and coloration, the color rendition being as nearly true as it is possible to obtain by professional photographic procedures.

DESCRIPTION OF THE NEW PLANT

The following is a detailed description of my new Alstroemeria plant as observed in greenhouse at Aalsmeer, Holland, with color designations according to The R.H.S. Colour Chart of The Royal Horticultural Society of London, England.

THE PLANT

Origin: Seedling.

Parentage:

*Seed parent.*—A breeding variety identified as Aur. or. 7.

*Pollen parent.*—A breeding variety identified as 0331-1. The plants employed in this crossing are identified in my records by the numbers stated and are at present included in my collection of Alstromeria plants for breeding purposes.

Classification:

*Botanic.*—Alstroemeria Hybrid.

*Commercial.*—Alstroemeria.

Form: An upright, erect bush.

Height: Up to about 200 cm. during a production season.

Main stem or cane length: Up to 150 to 200 cm., depending upon season.

Growth: Vigorous, strong and upright.

Root stock: Tuberous.

Foliage:

*Quantity.*—Average.

*Number of leaves.*—Depending upon season.

*Leaf shape.*—Elliptic with entire margins and acuminate apex.

*Leaf size.*—Length — About 15 to 20 cm. Width — About 3 cm.

*Texture.*—Leathery.

*Color.*—Upper side — Medium green. Under Side — Light green.

*Ribs and veins.*—Parallel from base to tip.

Rhizomes:

*Size.*—Various, increasing as season progresses.

*Color.*—White.

THE BUD

Form: Pear shaped.

Size: Medium.

*Diameter.*—About 1.5 cm.

*Length.*—About 4 cm.

Calyx: This plant has no calyx, the six petals of the flower being perianth and dividing simultaneously.

Peduncle:

*Length.*—About 9 cm.

*Color.*—Green.

THE FLOWER

Blooming habit: Continuous during the entire blooming season.

Flower size: Very large.

*Diameter.*—About 6 cm.

*Depth.*—About 6 cm.

Borne: Singly.

Shape or Form: Cup-shaped with the petals curling outward as the bloom matures.

Petalage:

*Number of petals.*—Six.

*Arrangement.*—Two concentric groups of three petals each.

*Form.*—Outer petals — Obovate with mucronate apex. Inner petals — Elliptic with entire margins and narrow apex.

*Texture.*—Leathery.

*Appearance.*—Satiny.

*Color.*—Outer petals — 45 A on both upper side and under side. Inside petals: Contiguous upper pair: Middle body portion — 21 A. Upper half of length — 45 A. Base — 33 A. Reverse side — 44 A. Pencil stripes lengthwise from base to apex.

Peduncle:

*Length.*—About 3 cm.

*Character.*—Strong and upright.

*Color.*—Green.

Persistence: The flowers hang on and dry.

Lasting quality:

*On the plant.*—About twenty-one days.

*As a cut flower.*—About fourteen days in vase keeping.

THE REPRODUCTIVE ORGANS

Stamens:

*Number.*—Six.

*Arrangement.*—One opposite each petal.

*Anthers.*—Size: About 10 mm. Color: Red/Black.

*Filaments.*—Length: About 5 cm. Color: Light red.

*Pollen.*—Color: Black.

Pistils:

*Number.*—One.

Style:

*Length.*—About 4 cm.

*Color.*—Light red.

*Stigma.*—Color: Light red.

I claim:

1. The new and distinctive Alstroemeria plant and parts thereof, substantially as herein shown and described, distinguished by the very large size of its blooms and their soft red coloration and the yellow central body portion of the contiguous pair of inside petals, which have numerous, generally lengthwise-extending pencil stripes from base to tip.

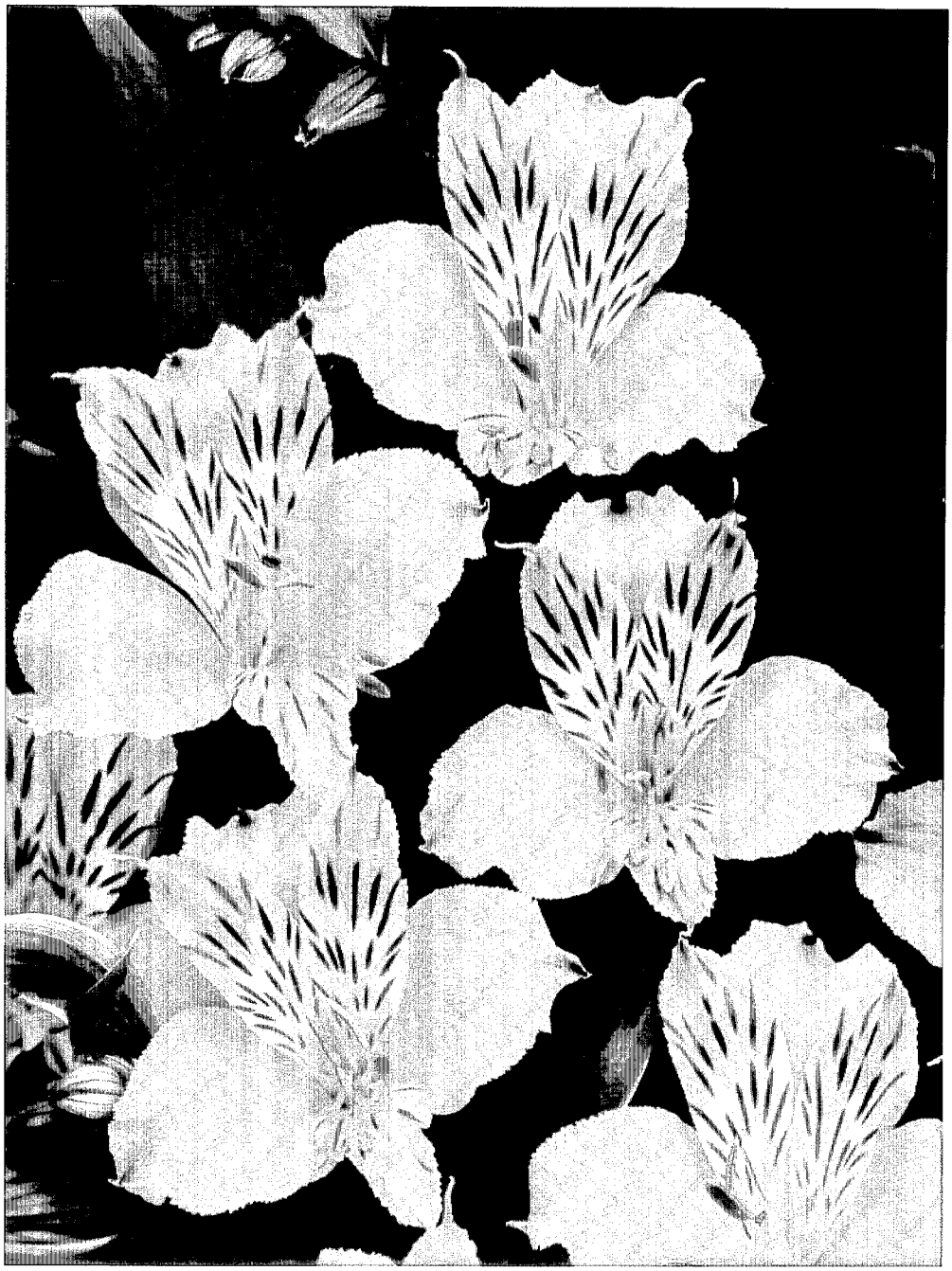

* * * * *